United States Patent [19]
Horrobin

[11] Patent Number: 5,264,217
[45] Date of Patent: Nov. 23, 1993

[54] METHOD OF INCREASING THE TOTAL FAT CONTENT OF MILK

[75] Inventor: David F. Horrobin, Guildford, England

[73] Assignee: Efamol Holdings Ltd., Surrey, England

[21] Appl. No.: 959,472

[22] Filed: Oct. 9, 1992

Related U.S. Application Data

[63] Continuation of Ser. No. 641,740, Jan. 15, 1991, abandoned.

[30] Foreign Application Priority Data

Jan. 30, 1990 [GB] United Kingdom ............... 9002048

[51] Int. Cl.$^5$ ............................................. A61K 31/20
[52] U.S. Cl. .................... 424/439; 514/558; 514/922
[58] Field of Search ........................ 424/439; 514/558

[56] References Cited

U.S. PATENT DOCUMENTS

| | | | |
|---|---|---|---|
| 4,867,986 | 9/1989 | Desai et al. | 424/439 |
| 4,970,076 | 11/1990 | Horrobin | 424/456 |
| 5,128,152 | 7/1992 | Horrobin et al. | 514/560 |

FOREIGN PATENT DOCUMENTS 1082624 9/1967
WO-A8810112 12/1988 PCT Int'l Appl.

OTHER PUBLICATIONS

American J Clinical Nutrition, vol. 32, 1979, pp. 304-312, G. Hall: "Uniformity of Human Milk".
Highlights Agric., vol. 28, No. 1, 1981, p. 15, M. Craig-Schmidt et al.: "Effect of Maternal Diet on Milk Composition."

*Primary Examiner*—Thurman K. Page
*Assistant Examiner*—Raj Bawa
*Attorney, Agent, or Firm*—Nixon & Vanderhye

[57] ABSTRACT

Methods for increasing the total fat and therefore energy content of mammalian and particularly human milk, the essential fatty acid content of that milk and the flow of that milk during lactation, or for preventing or reducing the normal decrease in milk fat content that occurs during prolonged lactation, by administering gamma linolenic acid, dihomo-gamma-linolenic acid or their mixture, alone or a physiologically acceptable diluent or carrier, in a form administrable to the lactating female.

13 Claims, No Drawings

METHOD OF INCREASING THE TOTAL FAT CONTENT OF MILK

This is a continuation of application Ser. No. 07/641,740, filed Jan. 15, 1991, now abandoned.

BACKGROUND

Breast feeding is the preferred method of feeding human infants, providing both energy and essential nutrients for the developing baby. As far as energy supply is concerned, fat is by far the most important constituent of milk. The fat also contains essential fatty acids (EFAs), vitamin-like essential nutrients which are extremely important in many aspects of human structure and function. EFAs seem to be particularly important for the developing brain, immunological system and cardiovascular system although they have roles to play in every organ in the body.

During prolonged breast feeding, the total fat and the EFA contents of human milk tend to fall progressively. These falls may limit the success of breast feeding and lead to an early requirement for supplementation with other foods. We have now discovered a method of reducing or preventing the fall of breast milk fat levels during prolonged breast feeding and of in many cases actually increasing both the total fat and the EFA content of human milk.

The outline of n-6 series fatty acid conversion in the body is:

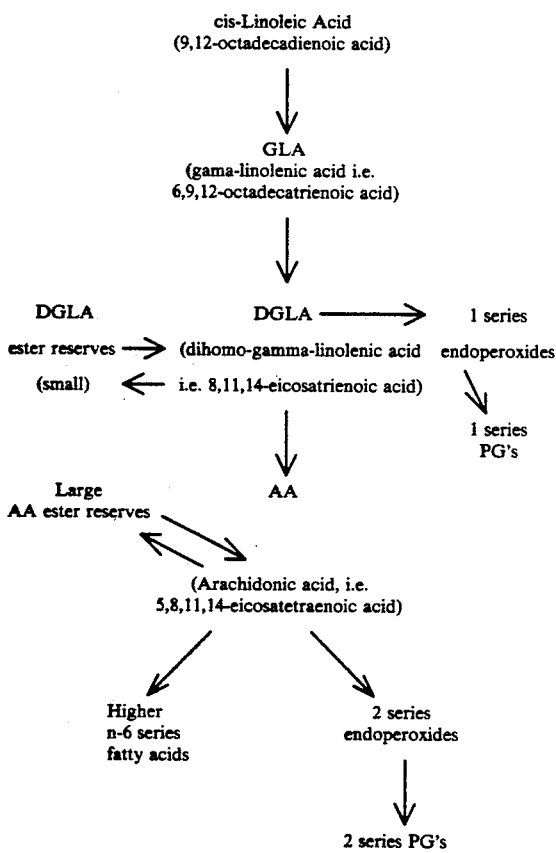

As appears from the chart, linoleic acid (LA) is the main n-6 EFA in the diet but in order to be useful to the body it must be converted first to gamma-linolenic acid (GLA) and then to further metabolites such as dihomo-gamma-linolenic acid (DGLA) and arachidonic acid (AA) which are precursors of 1 and 2 series prostaglandins respectively. GLA is very rapidly converted to DGLA and the two may be regarded as metabolically equivalent. However, the formation of GLA itself is slow and rate-limited by the 6-desaturase enzyme acting to generate it from LA. Similarly the conversion of DGLA to AA is also relatively slow.

EXPERIMENTAL

The production of breast milk and milk fat is stimulated by the hormone prolactin. Prolactin works in part by stimulating the formation of prostaglandin PGE1 from DGLA, and in view of the frequently slow production of its precursor GLA from linoleic acid in the body that the action of prolactin on the breast may be amplified by providing GLA or DGLA on which the stimulating mechanism can act. In a preliminary study in three nursing mothers GLA in the form of evening primrose oil appeared to stimulate the production of human milk fat. We therefore set up a placebo-controlled study in thirty six nursing mothers who wished to breast feed for a prolonged period: they had already completed three to four months feeding and aimed to continue for another eight months. Of this group, eighteen were given each day for eight months 8×500 mg capsules of evening primrose oil containing a total of 320 mg of GLA. The other eighteen were correspondingly given identical-appearing placebo capsules containing liquid paraffin.

At the beginning and end of the period a morning milk sample was collected from each mother. The total lipid was extracted and its amount measured. The fatty acids in the lipid were then converted to their methyl esters and analysed by gas chromatography. The results are shown in the accompanying table, in g/l ±SD:

TABLE 1

| Fatty Acid | Baseline | End | Change |
|---|---|---|---|
| On evening primrose oil | | | |
| Total fat | 44.26 ± 19.84 | 50.96 ± 28.37 | +15.1% |
| Linoleic | 5.86 ± 2.47 | 8.19 ± 5.12 | +39.8% |
| GLA + DGLA | 0.10 ± 0.05 | 0.22 ± 0.12 | +120% |
| Arachidonic | 0.26 ± 0.13 | 0.28 ± 0.16 | +7.7% |
| On placebo | | | |
| Total fat | 41.21 ± 11.75 | 31.83 ± 19.43 | −22.8% |
| Linoleic | 7.19 ± 2.94 | 5.21 ± 2.79 | −27.5% |
| GLA + DGLA | 0.18 ± 0.07 | 0.07 ± 0.04 | −61.1% |
| Arachidonic | 0.23 ± 0.12 | 0.17 ± 0.16 | −26.1% |

As can be seen, in the placebo group there was a decline both in the total fat level and in the levels of the individual EFAs in the milk. In contrast, in the GLA-treated group, not only was the decline prevented it was actually reversed. The GLA supplement increased both the total fat and the EFA content of the milk and especially the beneficial GLA/DGLA content. This effect in quality is significant, but since fat is the major source of energy in milk, the GLA supplement also substantially increased the total energy content of the milk.

The effect is not one of mere appearance of the supplement or its metabolites DGLA and AA in the milk, but a real effect on fat metabolism. This is shown by the linoleic acid content, given that in the body the conversions of linoleic acid to GLA, GLA to DGLA, DGLA to AA, and so on are not reversible.

Further, although not measured formally, we have had reports from several mothers that the milk flow increased substantially while taking evening primrose oil. GLA therefore stimulates milk flow as well as increasing EFA and total fat content.

STATEMENT OF INVENTION

The above discussion is in terms of human milk production but the physiology of milk production is similar in mammals generally and the invention is therefore applicable in veterinary practice where improvement of the fat quantity and composition and of the flow of milk is desired, and particularly in animal husbandry where cattle, sheep, goats or the like are kept for commercial milk production.

The invention therefore lies in a method of preparation of a medicament for increasing one or more of the total fat and therefore energy content of mammalian and particularly human milk, the EFA content of that milk and the flow of that milk, or for preventing or reducing the normal fall in milk fat content that occurs during prolonged lactation, wherein GLA and/or DGLA is provided, alone or in a physiologically acceptable diluent or carrier, in a form administrable to the lactating female.

Conveniently the medicament is suited to daily administration of 1 mg to 10 g of GLA and/or DGLA (such amount being the total if both are present) per 70 kg body weight, preferably 50 mg to 3 g, and very preferably 200 mg to 1.5 g, the medicament being in dosage unit form containing said amounts or sub-multiples thereof for oral, parenteral or other internal administration or as a topical preparation containing 0.01 to 20 weight % GLA and/or DGLA (said amount being the total if both are present) for application preferably to the mammae.

The invention also provides a method of increasing one or more of the total fat and therefore energy content of mammalian and particularly human milk, the EFA content of that milk and the flow of that milk, or for preventing or reducing the normal fall in milk fat content that occurs during prolonged lactation, wherein GLA and/or DGLA is administered to the lactating female, conveniently in the daily amounts and in the forms set out above.

DERIVATIVES OF EFAs

The acids may be used as such or as pharmaceutically acceptable and physiologically equivalent derivatives as for example detailed later herein and reference to any of the acids including reference in the claims is to be taken as including reference to the acids when in the form of such derivatives. Equivalence is demonstrated by entry into the biosynthetic pathways of the body as evidenced by effects corresponding to those of the acids themselves or their natural glyceride esters. Thus, indirect identification of useful derivatives is by their having the valuable effect in the body of the acid itself, but conversion for example of GLA to DGLA and on to AA can be shown directly by gas chromatographic analysis of concentrations in blood, body fat, or other tissue by standard techniques, for example those of Pelick et al, page 23, "Analysis of Lipids and Lipoproteins" Ed Perkins, American Oil Chemists Society, Champaign, Ill., U.S.A.

In outline the method is suitably that plasma samples (1 ml) are extracted with chloroform:methanol (2:1). The extract is filtered through sodium sulphate, evaporated to dryness, and taken up in 0.5 ml chloroform:methanol. The lipid fractions are separated by thin layer chromatography or silica gel plates. The phospholipid fraction, taken to reflect essential fatty acid contents most sensitively, is methylated using boron trifluoride-methanol. The resulting methyl esters of the fatty acids are separated and measured using a Hewlett-Packard 5880 gas chromatograph with a six foot column packed with 10% silar on chromosorb WAW 106/230. The carrier gas is helium (30 ml/min). Oven temperature is programmed to rise from 165° C. to 190° C. at 2° C./min. Detector temperature is 220° C. and injector temperature 200° C. Retention times and peak areas are automatically computed by Hewlett-Packard Level 4 integrator. Peaks are identified by comparison with standard fatty acid methyl esters.

DIETARY COMPOSITIONS

The invention is chiefly described in terms of medicaments and methods of treatment but it will be understood that the gamma-linolenic and other EFAs, being in the nature of dietary supplements, can be incorporated in a dietary margarine or other foodstuff or animal feed and such are to be understood as within the term pharmaceutical composition or medicament when used herein (including the claims).

FORMS AND SOURCES OF GAMMA-LINOLENIC AND OTHER ACIDS

Convenient physiologically equivalent derivatives of GLA and DGLA for use according to the invention include salts, amides, esters including glyceride esters and alkyl (e.g. $C_1$ to $C_4$) esters, and phospholipids.

If desired, pharmaceutical compositions may be produced for use in the invention by associating the natural or synthetic acids, as such or as derivatives, with an acceptable pharmaceutical vehicle. It is, however, at present convenient to provide at least GLA in the form of an available oil having a high GLA content, hence reference to "oils" herein.

One source of oils currently available is the seed of evening primrose species such as *Oenothera biennis L.* and *Oenothera lamarckiana,* the oil extract therefrom containing about 8% GLA and about 72% linoleic acid in the form of their glycerides, together with other glycerides (percentages based on total fatty acids). Other sources of GLA are borage species such as *Borago officinalis* which, though current yield per acre is low, provide a richer source than *Oenothera* oil. Oils from the seeds of members of the Ribes family are also often rich in GLA. Recent studies on fungi which can be cultivated by fermentation promise a fungal oil source, and chemical synthesis is also possible.

The oil is extracted from the seed by one of the conventional methods of extraction such as cold pressure, screw pressure after partially cooking the seed, or solvent extraction.

Fractionation of a typical sample of this oil in the form of methyl esters shows the relative proportions:

| Palmitate | 6.15 |
| --- | --- |
| Stearate | 1.6 |
| Oleate | 10.15 |
| Linoleate | 72.6 |
| Gamma-linolenate | 8.9 |

The seed oil extracts referred to above can be used as such or can, for example, if desired, be fractionated to yield an oily composition containing the triglycerides of gamma-linolenic and linoleic acids as the main fatty acid components, the gamma-linolenic acid content being, if desired, a major proportion. Seed oil extracts appear to have a stabilising effect upon DGLA if present.

If DGLA is to be used it can be prepared by chemical synthesis or by fungal fermentation.

PHARMACEUTICAL PRESENTATION

As mentioned briefly above, the compositions are conveniently in a form suitable for oral, rectal, parenteral or other internal administration in a suitable pharmaceutical vehicle, as discussed in detail, for example, in Williams British Patent Specification No. 1,082,624, to which reference may be made, and in any case very well known generally for any particular kind of preparation. Thus, for example, tablets, capsules, ingestible liquid or powder preparations can be prepared as required, and topical preparations also when the gamma-linolenic acid or other acids are absorbed through the skin. Injectable solutions of hydrolysed Oenothera oil may be prepared using albumin to solubilise the free acid.

Advantageously, a preservative is incorporated into the preparation. Alpha-tocopherol in concentration of about 0.1% by weight has been found suitable for the purpose and is one of a number of possible stabilisers well known in the field and including also for example ascorbyl palmitate and stearate.

It will be understood that the absolute quantity of active materials present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

EXAMPLES

The following may be given to nursing mothers for increasing the total fat and therefore energy content of breast milk:

1. 8×500 mg capsules per day evening primrose oil (containing 8% GLA by weight).
2. 6×1 g capsules per day borage oil (containing 22% GLA by weight).
3. 8×500 mg capsules per day blackcurrent seed oil (containing 18% GLA by weight).
4. 6×500 mg capsules per day oil of microbial origin from the fungi Mortierella or Rhizopus containing 20% GLA by weight. (The biomass of suitable strains contains ca. 15% oil by weight of which 15 to 20% is GLA).
5. 6×500 mg capsules per day oil of such microbial origin containing 19% of DGLA by weight.
6. 2×250 mg capsules per day purified GLA in triglyceride, free fatty acid, methyl ester or ethyl ester form.
7. 2×300 mg capsules per day DGLA in triglyceride, free fatty acid, methyl or ethyl ester form.
8. Cream for application to the breasts containing 20% evening primrose oil by weight.
9. Cream for application to the breasts containing 2% of purified GLA or DGLA by weight.
10. In animal husbandry corresponding amounts of GLA or DGLA related to body weight may be given, for example GLA may be used in the form of evening primrose seed cake residue (3% residual oil of which 9% is GLA), or as crushed evening primrose, borage or blackcurrant seeds, or as microbial biomass, for example:

a. A cake for feeding to cattle containing 2% by weight of evening primrose seed cake.
   b. A cake for feeding to cattle containing 1% by weight of crushed borage seed Borago officinalis (24% oil, of which 21% is GLA).
   c. A cake for feeding to goats containing 0.5% by weight of GLA-rich microbial biomass, Mortierella or Rhizopus as above.

I claim:

1. A method for increasing the total fat content of mammalian milk, the essential fatty acid content of mammalian milk or the flow of mammalian milk during lactation, said method comprising administering to a lactating female mammal from 1 mg to 10 g of gamma-linolenic acid, dihomo-gamma-linolenic acid or mixtures thereof per 70 kg body weight, alone or in a physiologically acceptable diluent or carrier.

2. The method of claim 1 wherein from 1 mg to 10 g of gamma-linolenic acid, dihomo-gamma-linolenic acid or their mixture is administered per 70 kg body weight.

3. The method of claim 1 wherein the amount administered is 50 mg to 3 g per 70 kg body weight.

4. The method of claim 3 wherein the amount administered is 200 mg to 1.5 g per 70 kg body weight.

5. The method of claim 1 wherein the gamma-linolenic acid, dihomo-gamma-linolenic acid or mixture is administered orally or parenterally.

6. A method for increasing the total fat content of mammalian milk, the essential fatty acid content of mammalian milk or the flow of mammalian milk during lactation, said method comprising topically applying to the skin of a lactating female mammal a topical composition containing 0.901 to 20 weight percent gamma-linolenic acid, dihomo-gamma-linolenic acid or mixtures thereof, in a physiologically acceptable topical carrier.

7. The method of claim 6 wherein the topical composition is applied to the mammae.

8. A method for preventing or reducing the decrease in milk fat content that occurs during prolonged lactation, said method comprising administering to a lactating female mammal 1 mg to 10 g of gamma-linolenic acid, dihomo-gamma-linolenic acid or mixtures thereof per 70 kg body weight, alone or in a physiologically acceptable diluent or carrier.

9. The method of claim 8 wherein the amount administered is 50 mg to 3 g per 70 kg body weight.

10. The method of claim 9 wherein the amount administered is 200 mg to 1.5 g per 70 kg body weight.

11. The method of claim 8 wherein the gamma-linolenic acid, dihomo-gamma-linolenic acid or mixture is administered orally or parenterally.

12. A method for preventing or reducing the decrease in milk fat that occurs during prolonged lactation, said method comprising topically administering to a lactating female mammal a topical composition containing 0.901 to 20 weight percent gamma-linolenic acid, dihomo-gamma-linolenic acid or mixtures thereof, alone or in a physiologically acceptable topical carrier.

13. The method of claim 12 wherein the topical composition is applied to the mammae.

* * * * *